United States Patent
Saussaye et al.

(10) Patent No.: US 10,188,799 B2
(45) Date of Patent: Jan. 29, 2019

(54) AUTOINJECTOR

(71) Applicant: APTAR FRANCE SAS, Le Neubourg (FR)

(72) Inventors: Anthony Saussaye, Saint Sulpice sur Risle (FR); Olivier His, Saint Etienne du Vauvray (FR)

(73) Assignee: APTAR FRANCE SAS, Le Neubourg (FR)

( * ) Notice: Subject to any disclaimer, the term of this patent is extended or adjusted under 35 U.S.C. 154(b) by 101 days.

(21) Appl. No.: 15/100,395

(22) PCT Filed: Apr. 9, 2015

(86) PCT No.: PCT/FR2015/050934
§ 371 (c)(1),
(2) Date: May 31, 2016

(87) PCT Pub. No.: WO2015/155482
PCT Pub. Date: Oct. 15, 2015

(65) Prior Publication Data
US 2016/0303323 A1  Oct. 20, 2016

(30) Foreign Application Priority Data
Apr. 11, 2014 (FR) ..................... 14 53228

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3157* (2013.01); *A61M 5/326* (2013.01);
(Continued)

(58) Field of Classification Search
CPC .. A61M 5/2033; A61M 5/5086; A61M 5/326; A61M 5/3157; A61M 2205/584; A61M 2005/206; A61M 2005/2013
See application file for complete search history.

(56) References Cited

U.S. PATENT DOCUMENTS

| 7,141,286 | B1 * | 11/2006 | Kessler | ............... A61M 5/3202 |
| | | | | 428/41.8 |
| 2009/0270804 | A1 * | 10/2009 | Mesa | ................... A61M 5/2033 |
| | | | | 604/111 |
| 2009/0326479 | A1 * | 12/2009 | Janish | ................ A61M 5/31511 |
| | | | | 604/218 |

FOREIGN PATENT DOCUMENTS

| EP | 2 716 318 A1 | 4/2014 |
| WO | 2005/097238 A2 | 10/2005 |

(Continued)

OTHER PUBLICATIONS

International Search Report for PCT/FR2015/050934 dated Jul. 13, 2015.
(Continued)

*Primary Examiner* — Bradley J Osinski
(74) *Attorney, Agent, or Firm* — Sughrue Mion, PLLC

(57) ABSTRACT

An autoinjector having a body to receive a reservoir and an actuator sleeve including a contact end and extending inside the body and movable relative to the body between projecting positions and an actuated position. The actuator sleeve is in a first projecting position before actuation of the autoinjector and in a second projecting position after actuation. The actuator sleeve, in the second projecting position, extends axially further out from the body than in the first projecting position and includes an annular zone that, in the first projecting position, is arranged inside the body and in the second projecting position is arranged outside the body. The annular zone includes a visual indicator that the auto- (Continued)

Figure 1:
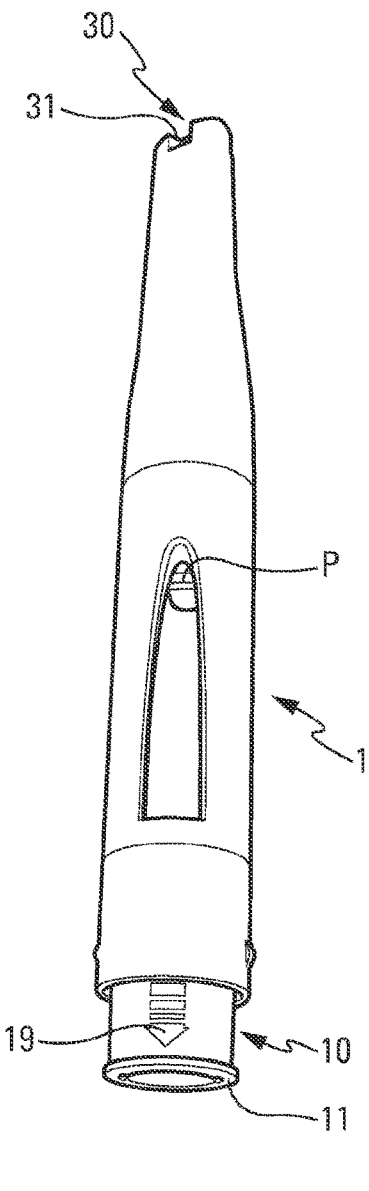

injector has been actuated. Axially adjacent the annular zone the actuator sleeve includes a shoulder, projecting radially outwards relative to the visual indicator, thereby protecting the indicator against contact with the inside of the body.

9 Claims, 3 Drawing Sheets

(51) Int. Cl.
    *A61M 5/32*     (2006.01)
    *A61M 5/50*     (2006.01)

(52) U.S. Cl.
    CPC ..... *A61M 5/5086* (2013.01); *A61M 2005/206* (2013.01); *A61M 2005/2013* (2013.01); *A61M 2205/584* (2013.01)

(56) References Cited

FOREIGN PATENT DOCUMENTS

| WO | 2012/045350 A1 | 4/2012 |
|----|----------------|--------|
| WO | 2012/072568 A1 | 6/2012 |
| WO | 2014/053378 A2 | 4/2014 |

OTHER PUBLICATIONS

International Preliminary Report on Patentability issued from the International Bureau in counterpart International Application No. PCT/FR2015/050934.

\* cited by examiner

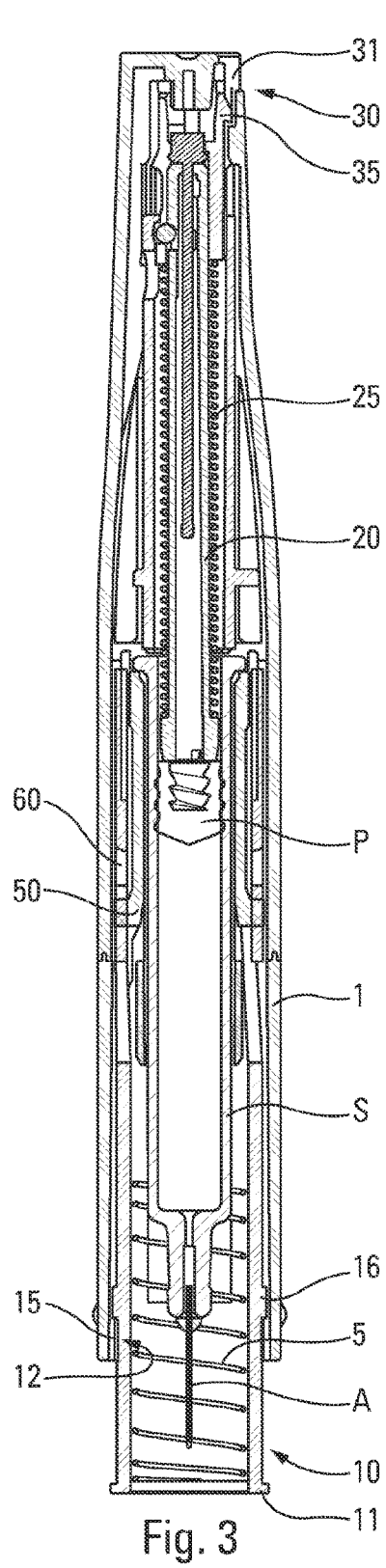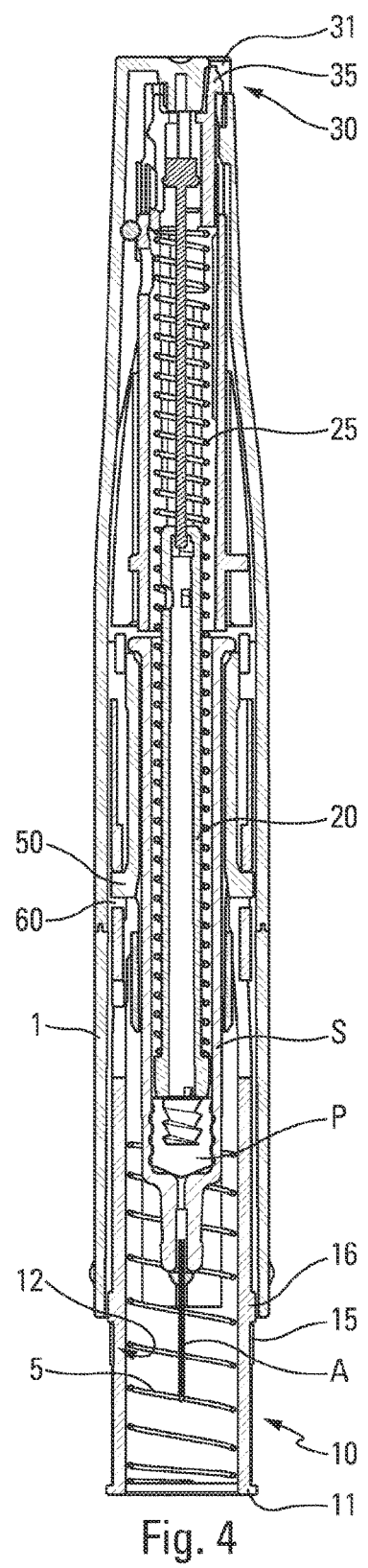

AUTOINJECTOR

CROSS REFERENCE TO RELATED APPLICATIONS

This application is a National Stage of International Application No. PCT/FR2015/050934 filed Apr. 9, 2015, claiming priority based on French Patent Application No. 1453228 filed Apr. 11, 2014, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the injection of the fluid contained in the syringe automatic. Autoinjectors are relatively complex devices that must satisfy a certain number of constraint requirements in order to be reliable. The robustness of the device, its handling, and its ease of use for the user are also important elements. In particular, it is important for the user to be able to identify easily and clearly whether the autoinjector is ready for use or, on the contrary, that it has already been used. This information may be crucial in an emergency. In addition, since most autoinjectors are for single use, the cost of manufacture and of assembly is also a factor that needs to be taken into account.

Documents WO 2005/097238 and WO 2012/045350 describe prior-art devices.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that clearly informs the user that the autoinjector has already been used.

Another object of the present invention is to provide an autoinjector that is simple and inexpensive to manufacture and to assemble.

The present invention thus provides an autoinjector comprising a body that is adapted to receive a reservoir, said reservoir containing fluid and including a piston and a needle, such as a pre-filled syringe, said autoinjector further comprising an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector; said actuator sleeve, in said second projecting position, extending axially further out from said body than in said first projecting position, said actuator sleeve including an annular zone that, in said first projecting position, is arranged inside said body and that, in said second projecting position, is arranged outside said body, said annular zone including a visual indicator for indicating to the user that the autoinjector has been actuated; and axially adjacent to said annular zone, said actuator sleeve including an outwardly-projecting radial shoulder, said shoulder projecting radially outwards relative to said visual indicator, thereby protecting said visual indicator against any contact with the inside surface of the body while the actuator sleeve is moving in said body, the bottom end of the actuator sleeve, that comes into contact with the zone in which injection takes place, also including an outwardly-projecting radial shoulder.

Advantageously, said shoulder is formed by a peripheral radial projection.

In a variant, said shoulder is formed by two or more radial projections that are distributed around the periphery of said actuator sleeve.

Advantageously, said visual indicator is formed by a self-adhesive label that is applied to the outside surface of said actuator sleeve, at least to said annular zone.

Advantageously, in said second projecting position, said actuator sleeve is locked in position by tabs that are secured to the body or to the reservoir, and that co-operate with openings in said actuator sleeve.

Advantageously, said autoinjector includes a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position.

Advantageously, the radially-outer surface of said shoulder is smooth, so as to limit possible friction with the inside surface of the body while said actuator sleeve is moving in said body.

Advantageously, said actuator sleeve further includes an information indicator that can be seen in said first projecting position of the actuator sleeve.

Figure 2:
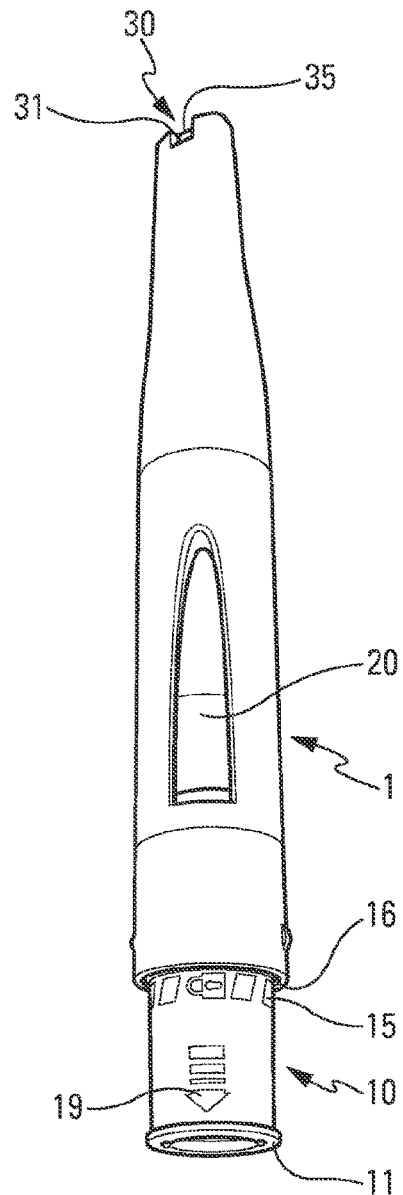
Figure 5:
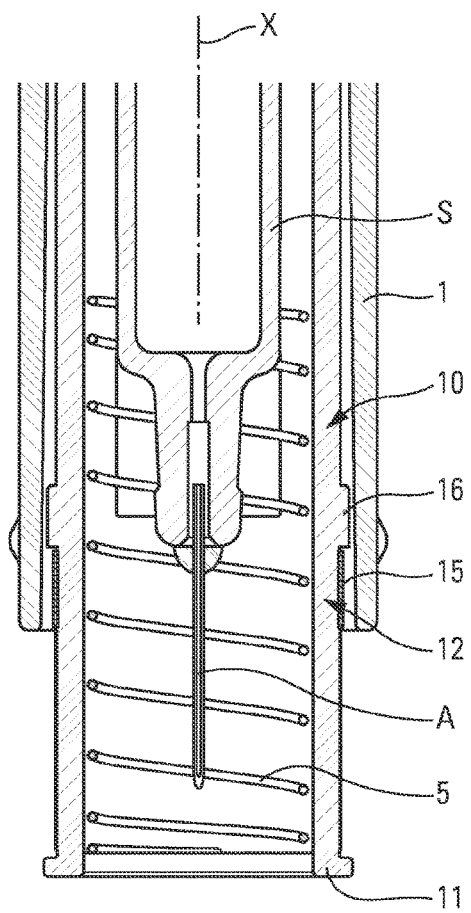
Figure 6:
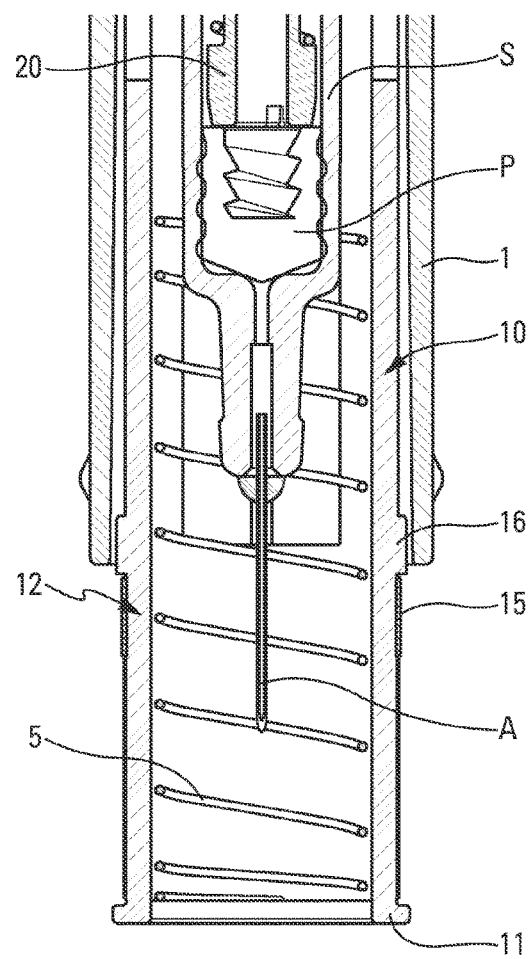

These characteristics and advantages, and others, of the present invention appear more clearly from the following detailed description, given by way of non-limiting example, and with reference to the accompanying drawings, in which:

FIGS. 1 and 2 are side views of an autoinjector in an advantageous embodiment, respectively before and after injection;

FIGS. 3 and 4 are diagrammatic section views of an autoinjector in an advantageous embodiment, respectively before and after injection; and FIGS. 5 and 6 are views of a detail of FIGS. 3 and 4 respectively.

In the following description, the terms "top" and "bottom" refer to the positions shown in the figures. The terms "axial" and "radial" refer to the longitudinal central axis X shown in FIG. 5.

The autoinjector is described below with reference to an advantageous embodiment. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 11 that is for coming into contact with the body of the patient around the injection zone.

A reservoir S may be inserted into said autoinjector. The reservoir S contains fluid and includes a piston P and a needle A. The piston P is adapted to move in said reservoir S so as to inject the fluid through said needle A.

The present description is made with reference to a syringe S that may be of any type. More generally, it is understood that the term "syringe" in the present description encompasses any type of reservoir associated with a needle. Preferably, the reservoir S is a pre-filled syringe.

Before actuation, the actuator sleeve 10 is in a first projecting position in which it surrounds the needle A, as shown in FIGS. 1, 3, and 5. During actuation, the actuator sleeve 10 slides inside the body 1 towards an actuated position, so as to expose the needle A and enable pricking, and then injection of the fluid. After injection, the actuator sleeve 10 returns into a second projecting position in which it is once again arranged around the needle A, so as to avoid any risk of injury with said needle, as shown in FIGS. 2, 4, and 6. The actuator sleeve 10 is advantageously urged towards its projecting positions by a spring 5 that may be of any type.

The autoinjector also comprises an automatic injection system, in particular comprising a piston rod 20 that is adapted to co-operate with the piston P so as to move it in the reservoir S so as to dispense the fluid through the needle A. Conventionally, the piston rod 20 is urged by a spring 25 towards its dispensing position and, before actuation, it is held in its rest position by an appropriate injection lock. A visual and/or sound indication device 30 may be provided at the top end of the body 1 of the autoinjector, with one or more slots 31 adapted to receive an indicator 35 after injection, visible through the slot(s) 31. The various modules or systems (automatic injection system, injection lock, visual and/or sound indication device) that are not essential to the operation of the present invention are not described in greater detail below. They could be made in ways that are different to the particular embodiment shown in the drawings. In particular, they could be made in accordance with the teachings of documents WO 2013/175148 or US 2014/088505.

In the invention, when it is in its second projecting position after injection, said actuator sleeve 10 axially extends further out from said body 1 than in said first projecting position before actuation. Thus, said actuator sleeve 10 includes an annular zone 12 that, in said first projecting position, is arranged inside said body 1 and that, in said second projecting position, is arranged outside said body 1. The annular zone 12 includes a visual indicator 15, such as a specific marking, that informs the user that the autoinjector has already been used. The visual indicator 15 may be of any type, e.g. color(s), and/or may include symbols, letters, or words, or any other marking that can be easily identified by the user. The visual indicator 15 may be applied to said annular zone 12 by any appropriate means, e.g. via a self-adhesive label adhesively-bonded on the outside surface of the actuator sleeve 10. Other means may be envisaged for making said visual indicator 15.

Advantageously, in said second projecting position after injection, said actuator sleeve 10 is locked, and can no longer be moved axially into said body 1. By way of example, locking may be achieved by tabs 50 that are secured to the body 1 or to the reservoir S, and that co-operate with openings 60 in said actuator sleeve 10 when said actuator sleeve reaches its second projecting position.

In the embodiment in FIGS. 3 and 4, the tabs 50 are secured to the reservoir S. The visual indicator 15 may thus include means that identify such locking, e.g. a padlock in the embodiment in FIG. 2.

In an aspect of the invention, axially adjacent to said annular zone 12 towards said body 1, said actuator sleeve 10 includes a shoulder 16 that projects radially outwards. Advantageously, the shoulder 16 is completely inside said body 1 in said first projecting position of the actuator sleeve before injection, as can be seen clearly in FIGS. 3 and 5. In said second projecting position after injection, said shoulder 16 is preferably also inside said body 1 at least in part, as shown in FIGS. 2, 4, and 6. The shoulder 16 may be a peripheral radial projection, or it may be formed by two or more radial projections that are distributed around the periphery of said actuator sleeve 10. The shoulder 16 thus projects radially outwards relative to said annular zone 12, and thus relative to said visual indicator 15. In this way, said visual indicator 15 is protected against any contact with the inside surface of the body 1 while the actuator sleeve 10 is moving in said body 1, initially from its first projecting position to its actuated position, then from its actuated position to its second projecting position. In the absence of the shoulder 16, the upwards and downwards movement of the actuator sleeve 10 in the body 1 could, by friction, spoil said visual indicator 15, in particular when said visual indicator is formed by a label that is adhesively-bonded on the outside surface of the actuator sleeve 10. The present invention thus guarantees an indication that is completely reliable for the user after using the autoinjector. Preferably, the radially-outer surface of said shoulder 16 is smooth, so as to limit possible friction with the inside surface of the body 1.

As shown in the drawings, the bottom end 11 of the actuator sleeve 10, that comes into contact with the zone in which injection takes place, also includes an outwardly-projecting radial shoulder. This implementation further protects the visual indicator, and in particular makes it easy to apply a self-adhesive label to the cylindrical outside surface of said actuator sleeve 10, between said shoulder 16 and said shoulder formed by said bottom end 11. The label may thus include said visual indicator 15 at said annular zone 12 that can be seen only in the second projecting position. Advantageously, the label may further include an information indicator 19 that can be seen in said first projecting position before injection, e.g. such as the arrow shown in FIG. 1, that indicates to the user in which direction it is necessary to press in order to actuate the autoinjector.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to an advantageous embodiment, naturally various modifications are possible for the person skilled in the art, without going beyond the ambit of the present invention, as defined by the accompanying claims.

The invention claimed is:

1. An autoinjector comprising a body that is adapted to receive a reservoir (S), said reservoir (S) containing fluid and including a piston (P) and a needle (A), said autoinjector further comprising an actuator sleeve that includes a contact end for coming into contact with a user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector; and wherein:

said actuator sleeve, in said second projecting position, extends axially further out from said body than in said first projecting position, said actuator sleeve including an annular zone that, in said first projecting position, is arranged inside said body and that, in said second projecting position, is arranged outside said body, said annular zone including a visual indicator for indicating to the user that the autoinjector has been actuated;

and, axially adjacent to said annular zone, said actuator sleeve includes an outwardly-projecting radial shoulder, said shoulder projecting radially outwards relative to said visual indicator, thereby protecting said visual indicator against any contact with an inside surface of the body while the actuator sleeve is moving in said body, a bottom end of the actuator sleeve, that comes into contact with a zone in which injection takes place, comprising an outwardly-projecting radial shoulder that projects radially outwards relative to said visual indicator and that is distinct from the outwardly-projecting radial shoulder that is axially adjacent to said annular zone.

2. An autoinjector according to claim 1, wherein said shoulder that is axially adjacent to said annular zone is formed by a peripheral radial projection.

3. An autoinjector according to claim 1, wherein said shoulder that is axially adjacent to said annular zone is formed by two or more radial projections that are distributed around a periphery of said actuator sleeve.

4. An autoinjector according to claim 1, wherein said visual indicator is formed by a self-adhesive label that is applied to an outside surface of said actuator sleeve, at least to said annular zone.

5. An autoinjector according to claim 1, wherein, in said second projecting position, said actuator sleeve is locked in position by tabs that are secured to the body or to the reservoir (S), and that co-operate with openings in said actuator sleeve.

6. An autoinjector according to claim 1, wherein said autoinjector includes a piston rod that is adapted to co-operate with the piston (P) of said reservoir (S), said piston rod being movable between a rest position and an injection position in which said piston rod has moved the piston (P) of the reservoir (S) so as to inject the fluid through the needle (A), an actuator spring being provided so as to urge said piston rod towards its injection position.

7. An autoinjector according to claim 1, wherein the radially-outer surface of said shoulder that is axially adjacent to said annular zone is smooth, so as to limit possible friction with the inside surface of the body while said actuator sleeve is moving in said body.

8. An autoinjector according to claim 1, wherein said actuator sleeve further includes an information indicator that can be seen in said first projecting position of the actuator sleeve.

9. The autoinjector according to claim 1, wherein said piston and said needle form part of a pre-filled syringe.

* * * * *